(12) United States Patent
Grimm et al.

(10) Patent No.: US 11,748,878 B2
(45) Date of Patent: Sep. 5, 2023

(54) METHODS AND SYSTEMS FOR GENERATING SURROGATE MARKER BASED ON MEDICAL IMAGE DATA

(71) Applicant: Siemens Healthcare GmbH, Erlangen (DE)

(72) Inventors: Robert Grimm, Nuremberg (DE); Berthold Kiefer, Erlangen (DE); Heinrich von Busch, Uttenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 361 days.

(21) Appl. No.: 16/992,379

(22) Filed: Aug. 13, 2020

(65) Prior Publication Data
US 2021/0049761 A1 Feb. 18, 2021

(30) Foreign Application Priority Data
Aug. 13, 2019 (DE) .......................... 102019212103.9

(51) Int. Cl.
*G06K 9/00* (2022.01)
*G06T 7/00* (2017.01)
(Continued)

(52) U.S. Cl.
CPC .............. *G06T 7/0012* (2013.01); *G06T 7/11* (2017.01); *G06T 7/62* (2017.01); *G16H 30/40* (2018.01);
(Continued)

(58) Field of Classification Search
CPC ........... A61B 5/055; A61B 5/20; A61B 5/416; A61B 5/4244; A61B 5/425; A61B 5/4381; A61B 5/4514; A61B 5/4519; A61B 6/03; G06T 2207/10081; G06T 2207/10088; G06T 2207/10116; G06T 2207/20081; G06T 2207/20084; G06T 2207/20124; G06T 2207/20161; G06T 2207/30056;
(Continued)

(56) References Cited

U.S. PATENT DOCUMENTS

| | | | | |
|---|---|---|---|---|
| 2004/0101181 | A1* | 5/2004 | Giger | ...................... G06T 7/187 382/128 |
| 2004/0267102 | A1* | 12/2004 | Skladnev | ............... A61B 5/442 382/128 |

(Continued)

FOREIGN PATENT DOCUMENTS

| | | |
|---|---|---|
| CN | 102207992 A | 10/2011 |
| CN | 103536360 A | 1/2014 |

(Continued)

OTHER PUBLICATIONS

European Search Report dated Apr. 17, 2020 for Application No. 10 2019 212 103.9.

*Primary Examiner* — Avinash Yentrapati
(74) *Attorney, Agent, or Firm* — Banner & Witcoff Ltd.

(57) ABSTRACT

In a method for generating a surrogate marker based on medical image data mapping an image region, the medical image data is detected using a first interface, a first subregion of the image region is selected by segmenting a first structure included in the image region, a first property of the first subregion is extracted, the surrogate marker is determined based on the first property, and the surrogate marker is provided using a second interface.

17 Claims, 4 Drawing Sheets

Figure 1:
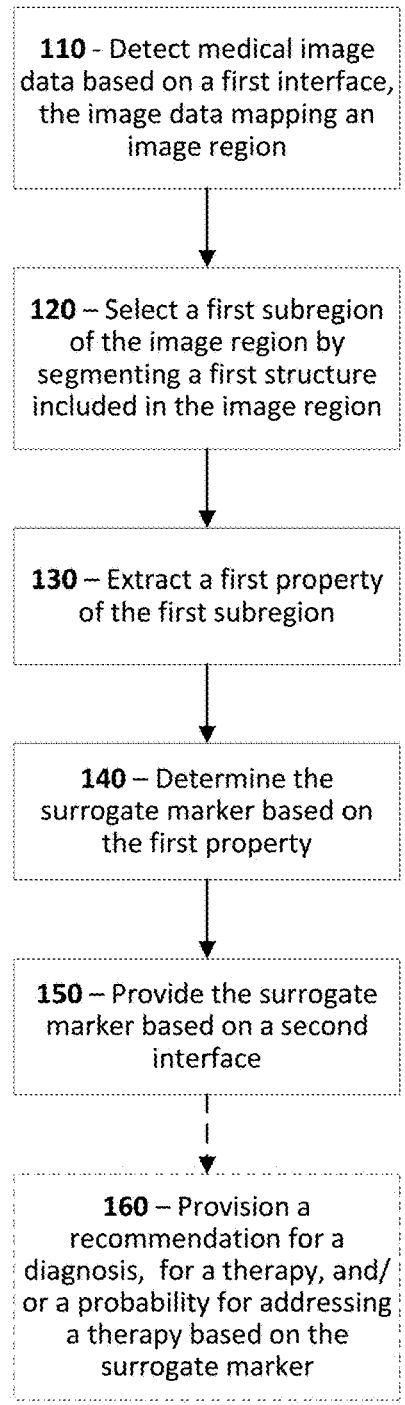

(51) Int. Cl.
*G06T 7/62* (2017.01)
*G16H 30/40* (2018.01)
*G16H 50/20* (2018.01)
*G06T 7/11* (2017.01)
*A61B 5/00* (2006.01)
*G16H 15/00* (2018.01)
*A61B 5/055* (2006.01)
*A61B 6/03* (2006.01)
*A61B 5/20* (2006.01)

(52) U.S. Cl.
CPC ............ *G16H 50/20* (2018.01); *A61B 5/055* (2013.01); *A61B 5/20* (2013.01); *A61B 5/416* (2013.01); *A61B 5/425* (2013.01); *A61B 5/4244* (2013.01); *A61B 5/4381* (2013.01); *A61B 5/4514* (2013.01); *A61B 5/4519* (2013.01); *A61B 6/03* (2013.01); *G06T 2207/20081* (2013.01); *G06T 2207/20084* (2013.01); *G06T 2207/20124* (2013.01); *G06T 2207/20161* (2013.01); *G06T 2207/30056* (2013.01); *G06T 2207/30081* (2013.01); *G06T 2207/30084* (2013.01); *G16H 15/00* (2018.01)

(58) Field of Classification Search
CPC . G06T 2207/30081; G06T 2207/30084; G06T 7/0012; G06T 7/11; G06T 7/149; G06T 7/62; G16H 15/00; G16H 30/40; G16H 50/20; G16H 50/30
See application file for complete search history.

(56) References Cited

U.S. PATENT DOCUMENTS

| | | | | |
|---|---|---|---|---|
| 2009/0028403 | A1* | 1/2009 | Bar-Aviv | G06T 7/0012 382/128 |
| 2010/0249580 | A1* | 9/2010 | Goto | A61B 5/1075 600/425 |
| 2011/0237938 | A1* | 9/2011 | Mizuno | G06T 7/187 600/425 |
| 2012/0188352 | A1* | 7/2012 | Wittenberg | A61B 90/361 348/E5.051 |
| 2014/0010428 | A1* | 1/2014 | Schmidt | A61B 5/0033 382/131 |
| 2015/0023578 | A1* | 1/2015 | Li | G06T 7/0012 382/131 |
| 2017/0116387 | A1* | 4/2017 | El-Zehiry | G16Z 99/00 |
| 2018/0122071 | A1* | 5/2018 | Bozorgtabar | G06T 7/0012 |
| 2018/0268569 | A1* | 9/2018 | Kroell | A61B 5/0037 |
| 2018/0360402 | A1 | 12/2018 | Carmi | |
| 2021/0049761 | A1* | 2/2021 | Grimm | G16H 30/40 |

FOREIGN PATENT DOCUMENTS

| | | |
|---|---|---|
| CN | 108472002 A | 8/2018 |
| CN | 108573487 A | 9/2018 |
| DE | 102009040430 B4 | 3/2013 |
| EP | 2030569 A1 | 3/2009 |
| JP | 2016198140 A | 12/2016 |

* cited by examiner

METHODS AND SYSTEMS FOR GENERATING SURROGATE MARKER BASED ON MEDICAL IMAGE DATA

CROSS REFERENCE TO RELATED APPLICATIONS

This patent application claims priority to German Patent Application No. 102019212103.9, filed Aug. 13, 2019, which is incorporated herein by reference in its entirety.

BACKGROUND

Field

The disclosure relates to a method, a provisioning system, a computer program product and an electronically readable data carrier for generating a surrogate marker based on medical image data.

Related Art

Medical image data involves two-dimensional image data records or three-dimensional volume data records of examination objects, which have been generated with imaging apparatuses, such as for instance magnetic resonance devices or computed tomography devices.

With this medical image data each pixel and/or voxel has a value which can be shown encoded as a gray-scale value or as color value, for instance as a two-dimensional layer, which is present in a three-dimensional volume data record. The pixel and/or voxel typically represents a signal intensity of a morphological and/or functional image. The medical image data typically maps a spatial section of the examination object, in particular an examination region, into pixels or voxels of this type, wherein the spatial section shown by the medical image data can be referred to as image region. The image region of the medical image data typically corresponds to the examination region of the examination object. Medical raw data which can be reconstructed to form the medical image data displaying the image region is typically acquired from the examination region.

In particular, medical image data generated by magnetic resonance devices can be morphological and/or functional and/or comprise different contrasts of the image region. Medical image data is evaluated by radiologists, who create a diagnosis with respect to the examination object based on contrasts, signal intensities, shape and/or size.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 1 a flowchart of a method according to an exemplary embodiment.

Figure 2:
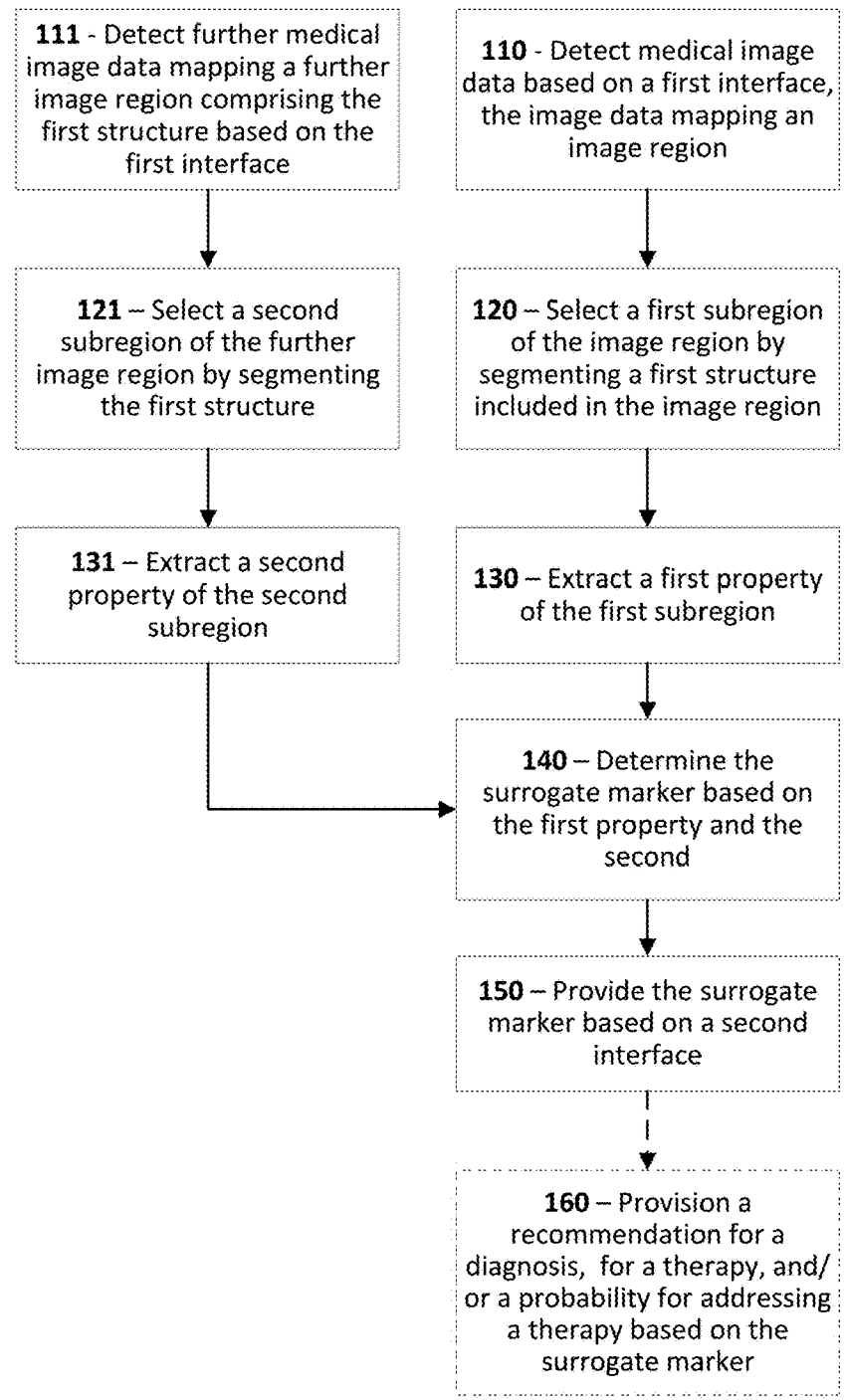

FIG. 2 a flowchart of a method according to an exemplary embodiment.

Figure 3:
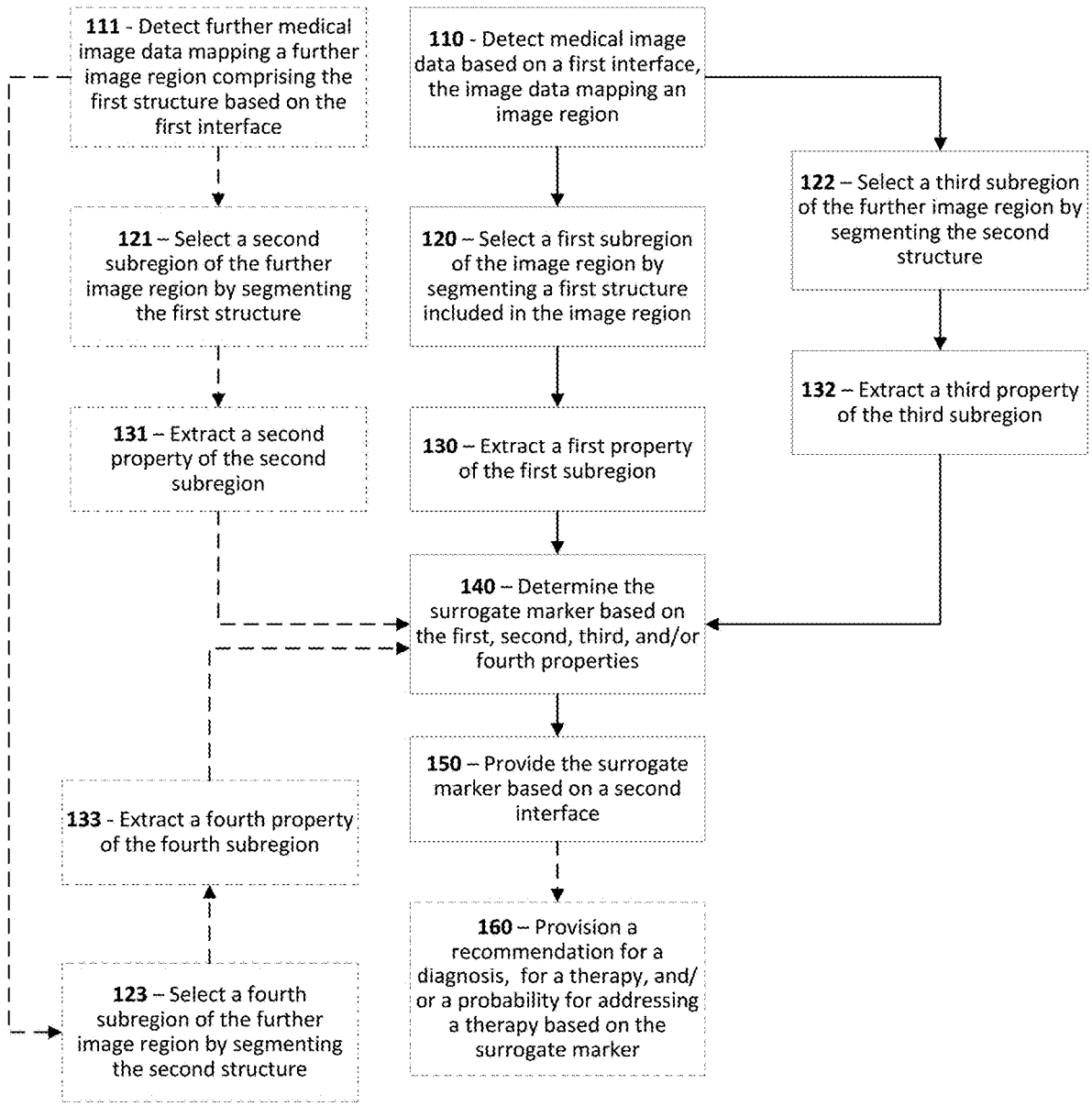

FIG. 3 a flowchart of a method according to an exemplary embodiment.

Figure 4:
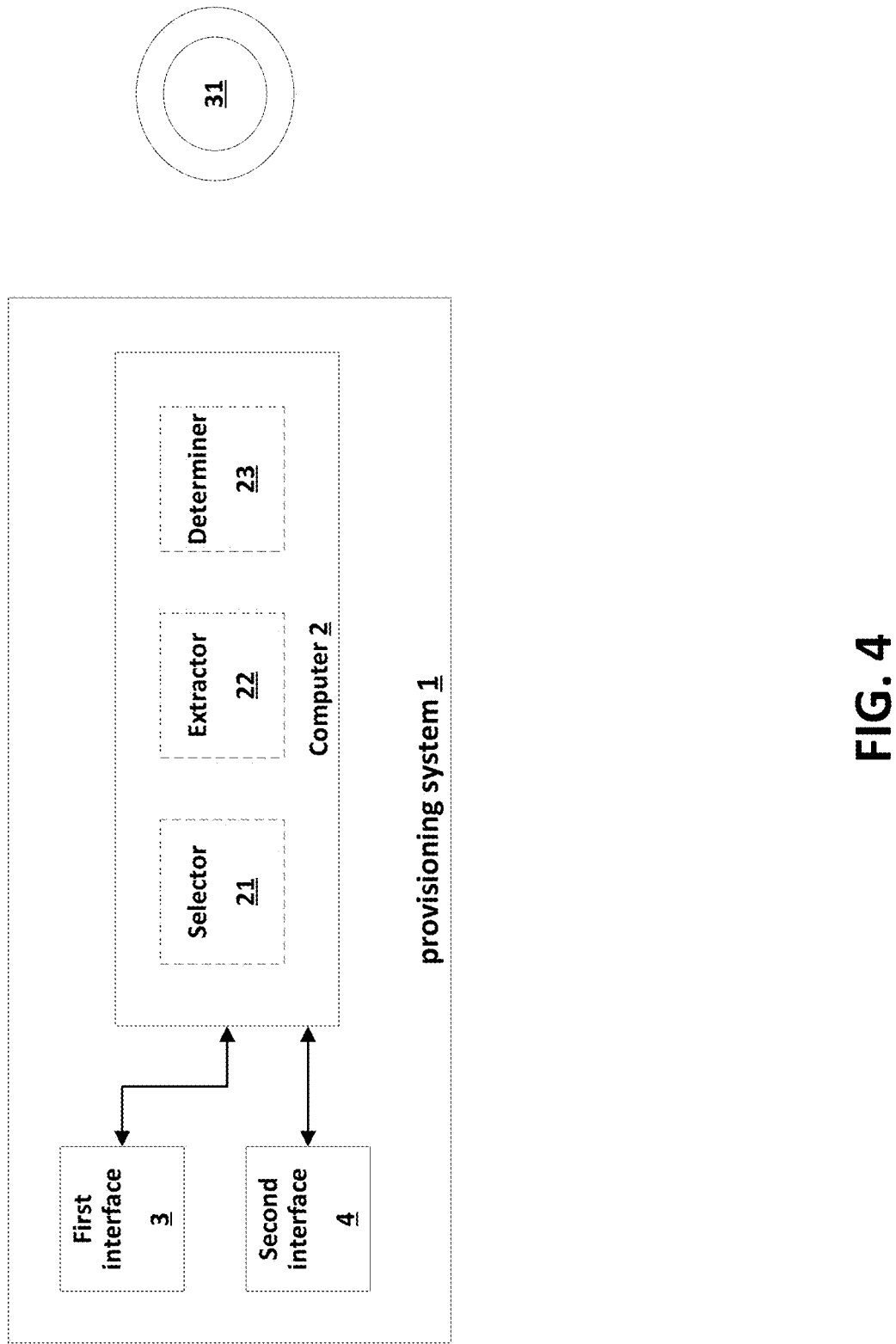

FIG. 4 a provisioning system according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

A surrogate marker is a measured value which is used to assess a health situation of an examination object, in particular of a patient. In particular, a surrogate marker can characterize an effect of a therapy and/or the progress of an illness. A statistically significant association typically exists between the surrogate marker and a symptom and/or a disease.

The object underlying the disclosure is to specify a particularly precise and robust method for generating a surrogate marker based on medical image data.

The inventive method for generating a surrogate marker based on medical image data mapping an image region provides the following method steps:

detecting the medical image data on the basis of a first interface, selecting a first subregion of the image region by segmenting a first structure included in the image region, extracting a first property of the first subregion, determining the surrogate marker based on the first property, providing the surrogate marker on the basis of a second interface.

The detection of the medical image data on the basis of the first interface typically comprises a provisioning of the medical image data. The medical image data preferably has a data format, which is provided for the inventive method, in particular by way of the first interface. The medical image data was preferably generated in advance by a medical imaging device, in particular a magnetic resonance device and/or computed tomography device and/or x-ray device. The detection of the medical image data can also comprise an acquisition of the medical image data, in particular an acquisition of medical raw data and reconstruction of medical image data from the medical raw data.

The first structure is typically a structure and/or a shape within the examination region of the examination object. The image region typically comprises the first structure in its entirety. The first subregion is typically included in the image region. The first subregion typically encloses the first structure in a flush and/or accurately-fitting manner. The first subregion typically encloses a portion of the image region.

The first property preferably comprises a feature and/or an item of information relating to the medical image data within the first subregion and/or restricted to the first subregion.

The first property typically comprises an item of image information included in the medical image data within the first subregion and/or restricted to the first subregion. The extraction of a first property of the first subregion typically comprises a determination of the first property based on the first subregion of the medical image data.

The determination of the surrogate marker based on the first property typically takes into account the first subregion of the medical image data and the first property. When the surrogate marker is determined, a database comprising an association between the surrogate marker and the first property is preferably. The surrogate marker is preferably quantitative. The first property is preferably quantitative.

The association between the surrogate marker and the first property is preferably determined by a function. The association between the surrogate marker and the first property is preferably based on data records in each case comprising a first property and knowledge of at least 10, preferably at least 100, particularly preferably at least 1000 examination objects resulting from the first property. The knowledge resulting from the first property can be a diagnosis and/or a measure of an illness and/or a measure of the effectiveness of a therapy. The knowledge resulting from the first property can be the surrogate marker. The determination of the surrogate marker based on the first property typically takes place automatically. The extraction of the first property typically takes place automatically. The selection of a first subregion typically takes place automatically.

In an exemplary embodiment, the provision of the surrogate marker comprises outputting the surrogate marker by way of the second interface. The first interface can correspond to the second interface.

The advantage of the inventive method lies therein in the surrogate marker being able to determine particularly objectively. In particular, it is possible to dispense with a manual and/or subjective determination, since the selection of the first subregion and/or the extraction of the first property and/or the determination of the surrogate marker is free of subjective evaluations. As a result, the surrogate marker can be determined particularly reproducibly independently of the attending physician, as a result of which the method is particularly precise and/or robust. The state of health of the examination object, based on which medical image data the surrogate marker is determined, can be determined particularly accurately from a precise and objectively determined surrogate marker of this type. This enables an illness to be identified earlier and/or improved planning of a therapy and/or an improved prediction of an effectiveness of a therapy and/or an improved prediction about a future course of an illness of the examination object. Treatment costs can be reduced as a result and/or the probability of a cure can be increased. Similarly, a diagnosis can be made more quickly since the provisioning of medical image data is adequate.

In an exemplary embodiment, the selection of the first subregion takes place by applying a trained function and/or a neural network and/or an active shape model and/or a level-set method to the medical image data, and/or a machine-learning algorithm.

If the selection of the first subregion comprises the application of a neural network for segmenting the first structure, the neural network was preferably trained in advance. The neural network was preferably trained in advance on the basis of a plurality of medical image data comprising the first structure, wherein the first structure was provided in segmented form for the plurality of medical image data in each case. This embodiment enables a particularly precise segmentation of the first structure, as a result of which the surrogate marker can be determined particularly accurately.

One embodiment of the method provides that the method involves providing a recommendation for a diagnosis and/or for a therapy and/or a probability for addressing a therapy based on the surrogate marker. The provisioning can take place visually and/or by creating a report, for instance. This embodiment enables the physician to be assisted when making a diagnosis and/or deciding on a therapy. This allows for a more objective diagnosis and for an improved treatment of the patient.

One embodiment of the method provides that the first structure has at least one of the following embodiments:
an organ
a substructure of an organ,
a prostate and/or a liver and/or a spleen and/or kidneys and/or pancreas,
a peripheral zone of the prostate,
a transition zone of the prostate,
a muscle and/or a cartilage.

If the first structure is an organ, it can in particular be an abdominal organ.

This embodiment provides for a selection for a first structure, wherein the first structure typically correlates with the surrogate marker to be determined. A peripheral zone of the prostate and/or a transition zone of the prostate as a first structure can be used for instance as a basis of a first property, which first property correlates with a surrogate marker indicating a tumor property and/or a tumor probability.

This embodiment enables a determination of different surrogate markers indicating different diagnoses and/or an effectiveness of different therapies, as a function of the first structure used.

One embodiment of the method provides that the first property has at least one of the following features:
a signal intensity within the first subregion,
a shape of the first subregion,
a volume of the first subregion,
an item of image information of the first subregion,
a diffusion value within the first subregion.

The medical image data typically comprises spatially resolved signal intensities, on the basis of which the first structure can be identified and/or a functionality within the first subregion is specified, for instance. An item of image information of the first subregion can comprise in particular a texture and/or a heterogeneity of a spatial distribution of the signal intensity within the first subregion. A diffusion value is typically extracted from medical image data, which was recorded by means of a magnetic resonance device and/or specifies an apparent diffusion coefficient (ADC value), as a first property. The first property of the first subregion typically establishes an association between the surrogate marker and the medical image data within the first subregion, in particular between the surrogate marker and the first structure.

This embodiment enables a determination of different surrogate markers indicating different diagnoses and/or an effectiveness of different therapies as a function of the first property used.

One embodiment of the method provides that the surrogate marker comprises at least one of the following features:
a symmetry property, a diameter,
a histogram,
a texture parameter,
a threshold value for a diffusion value,
threshold property,
a spatial distribution of a signal distribution,
a spatial distribution of a texture,
ratio of the first property to a threshold value.

In particular, if the first property comprises a shape of the first subregion, a symmetry property and/or a diameter can be determined as a surrogate marker. If the first property comprises a volume of the first subregion, a ratio of the first property to a threshold value and/or a threshold property can be determined as a surrogate marker. A threshold property is in particular a measure of a swelling, which can indicate an illness of the liver if the liver or the spleen is chosen as the first structure.

If the first property comprises a signal intensity and/or an item of image information and/or a diffusion value within the first subregion, a histogram and/or a texture parameter and/or a spatial distribution of the first property can be determined as a surrogate marker. The surrogate marker can comprise a feature of the first order, such as, for instance, a one-dimensional quantitative value. This can comprise in particular a statistical value with respect to the first subregion, such as, for instance, an average value, a standard deviation, a maximum, a minimum, and/or a homogeneity. In particular, the spatial distribution of a signal intensity can be defined on the basis of a spatial gradient and/or a heterogeneity. The surrogate marker can be a feature of the second order, such as, for instance, a two-dimensional or three-dimensional texture parameter.

In particular, spatial variations in a signal intensity within an organ and/or a substructure of an organ as a first structure can indicate an illness. If the spatial gradient of the signal intensity within the liver is above a defined threshold value here, this can be a surrogate marker for newly developing focal lesions. If the shape of the peripheral zone and/or the transition zone of the prostate is provided as the first property, for instance, an asymmetry of the first property can be considered to be a surrogate marker for a tumor. In particular, an asymmetry of the peripheral zone is an early indicator of a tumor as a surrogate marker.

The ratio of the first property to a threshold value can comprise a proportionality and/or a difference. The ratio of the first property to a threshold value can also be a binary value. Based on a diffusion value as a first property, the ratio of the diffusion value to a defined threshold value as a measure of the presence of a tumor can be used as a surrogate marker.

This embodiment enables, as a function of the first structure and the first property, a plurality of surrogate markers for quantifying an illness and/or an effectiveness of a therapy.

In this way the method can be used particularly flexibly.

One embodiment of the method provides that the method additionally comprises the following method steps:
detecting further medical image data mapping a further image region comprising the first structure on the basis of the first interface,
selecting a second subregion of the further image region by means of segmenting the first structure,
extracting a first property of the second subregion,
taking the second property into account when determining the surrogate marker.

The medical image data and the further medical image data both typically comprise the first structure of the same examination object. The medical image data and the further medical image data typically differ in terms of the time instant at which these were recorded. The medical image data and the further medical image data preferably only differ as a result of the time point at which these were recorded. The medical image data and the further medical image data were preferably recorded with a same recording technique.

The medical image data and the further medical image data is provided on the basis of a first interface. The medical image data and/or the further medical image data can also be acquired within the scope of a method step according to an embodiment of the inventive method.

The further image region and the image region preferably both comprise the first structure. The first subregion and the second subregion typically have an intersection. The intersection of the first subregion with the second subregion typically comprises at least 40%, preferably at least 60%, particularly preferably at least 80% of the first subregion.

The first subregion and the second subregion typically differ predominantly in terms of a change in the first structure on account of the time lag between the recording of the medical image data and the further medical image data.

A difference between the first property and the second property typically exists as a result of a temporal change in the first structure. When the surrogate marker is determined according to this embodiment, the first property and the second property is taken into account. In particular, the surrogate marker can be determined based on a difference between the first property and the second property.

This embodiment accordingly enables longitudinal medical image data to be taken into account. This enables a state of health of an examination object to be monitored. Changes between the first property and the second property can be quantified accordingly by the surrogate marker, as a result of which early identification of an illness is particularly efficient.

Similarly, an objective evaluation with respect to the significance of a therapy can take place and/or the need for a therapy can be evaluated. By taking a larger quantity of data into account, the surrogate marker can be determined more precisely.

The selection of the second subregion can take place similarly to the selection of the first subregion by applying a trained function and/or a neural network and/or an active shape model and/or a level-set method to the medical image data. The second property can comprise the features which were described for the first property. The second property can comprise another feature to the first property.

An embodiment of the method provides that the further image data was generated with a time lag from the image data. A period of time typically of at least one day, preferably of at least one week, particularly preferably of at least one month lies between the acquisition of the image data and the further image data. A period of time of at least one year can also lie between the acquisition of the image data and further image data.

This embodiment enables a continual monitoring of a therapy. This embodiment enables a continual monitoring of a progressing illness. This embodiment enables a longitudinal study of an examination object. This embodiment enables a surrogate marker to be identified and/or detailed precisely.

In an exemplary embodiment, the surrogate marker comprises at least one of the following features:
ratio of the second property to the first property, and/or ratio of the first property and/or the second property to at least one threshold value.

In an exemplary embodiment, the surrogate marker can also comprise a ratio of the second subregion to the first subregion. A ratio can be embodied as a difference and/or proportionality. This embodiment enables a particularly precise determination of a surrogate marker and/or prediction of an effectiveness of a therapy. For instance, the volume of the first subregion and the second subregion can be determined as a first property and second property, for instance. The surrogate marker can select a change in the volume and/or a change in the volume compared with a threshold value as a measure of a type of tumor illness. If a change in the volume of the peripheral zone of the prostate lies below a threshold value, for instance, the surrogate marker can indicate a benign tumor. If a change in the volume of the peripheral zone of the prostate lies above a threshold value, for instance, the surrogate marker can indicate a malign tumor.

One embodiment of the method provides that the method additionally comprises the following method steps:
- selecting a third subregion of the image region by segmenting a second structure included in the image region,
- extracting a third property of the third subregion,
- taking the third property into account when determining the surrogate marker.

The second structure differs from the first structure. The medical image data comprises the first structure and the second structure. The medical image data comprising the first structure and the medical image data comprising the second structure can be spatially separated from one another so that they comprise no shared image point. The medical image data comprising the first structure and the medical image data comprising the second structure can overlap at least partially. The medical image data comprising the first structure and the medical image data comprising the second structure are typically medical image data of the same examination object. The medical image data comprising the first structure and the medical image data comprising the second structure were typically recorded approximately at the same time as the examination object. The time instant of recording the medical image data comprising the first structure and the time instant of recording the medical image data comprising the second structure typically differ by at most two hours, preferably by at most one hour, particularly preferably by at most 30 minutes. The time instant of recording the medical image data comprising the first structure and the time instant of recording the medical image data comprising the second structure can also differ from one another by at most 20 minutes, preferably by at most 10 minutes.

The second structure can be a substructure of the first structure. The first structure and the second structure can be organs which differ from one another.

The first structure and the second structure can have a combination of two of the following embodiments, for instance:
- an organ
- a substructure of an organ,
- a prostate and/or a liver and/or a spleen and/or kidneys and/or pancreas,
- a peripheral zone of the prostate,
- a transition zone of the prostate,
- a muscle and/or a cartilage.

In particular, the first structure can be a prostate and the second structure a muscle. For instance, the first structure can be a liver and the second structure can be a spleen.

For instance, a diffusion value can be extracted from the first structure as a first property and a shape can be extracted from the second structure as a third property.

When the surrogator is determined, according to this embodiment the first property and the third property can be taken in account, as a result of which these can be particularly versatile and/or precise. A surrogate marker determined in this way is likewise particularly sensitive.

This embodiment can be combined with the consideration of the second property extracted from the second subregion of the further medical image data. If the further medical image data comprises the second structure, a selection of a fourth subregion of the further image region can take place by means of a segmentation of the second structure. Similarly, a fourth property can be extracted from the fourth subregion, which can be taken into account when the surrogate marker is determined.

In other words longitudinal medical image data and two structures which differ from one another can be taken into account when the surrogate marker is determined. This gives further details of the surrogate marker. A surrogate marker determined in this way can enable precise early recognition with respect to a special illness.

The selection of the third subregion can takes place similarly to the selection of the first subregion by applying a trained function and/or a neural network and/or an active shape model and/or a level set method to the medical image data. The third property can comprise the features which were described for the first property. The third property can comprise another feature as the first property. The second structure can comprise at least one of the embodiments described for the first structure. The second structure differs from the first structure. The selection of the fourth subregion can take place similarly to the selection of the first subregion by applying a trained function and/or a neural network and/or an active shape model and/or a level set method to the medical image data. The fourth property can comprise the features which were described for the first property. The fourth property can comprise another feature as the first property.

One embodiment of the method provides that the first subregion and the third subregion are disjointed. This makes it possible to take two separate organs into account. A surrogate marker determined in this way can take into account correlations between different structures particularly well and is particularly sensitive.

In an exemplary embodiment of the method provides that the medical image data comprising the first structure and the medical image data comprising the second structure were acquired on the basis of two recording methods, which differ at least by one parameter.

In an exemplary embodiment, the medical image data comprising the first subregion and the medical image data comprising the second subregion are acquired on the basis of two recording methods, which differ at least by one parameter.

In an exemplary embodiment, the parameter is a geometric parameter. The parameter can comprise, for example, a position of the examination object relative to the medical imaging device.

In an exemplary embodiment, the parameter can comprise a size of the subregion of the image region surrounding the first structure and a size of the subregion of the image region surrounding the second structure. The parameter can comprise a contrast parameter, for instance, which influences the contrast of the medical image data. A parameter determined on medical image data of this type can be particularly versatile and sensitive.

In an exemplary embodiment of the method provides that the surrogate marker comprises at least one of the following features:
 ratio of the third property to the first property, and/or
 ratio of the first property and/or the third property to at least one threshold value. The surrogate marker can also comprise a ratio of the third subregion to the first subregion. A surrogate marker of this type can enable a precise early recognition with respect to a special illness.

In an exemplary embodiment, the inventive method and/or aspects of the same are computer-implemented methods.

Furthermore, the disclosure is based on a provisioning system comprising a first interface, which is configured to detect medical image data, a second interface, which is configured to provide a surrogate embodied marker, and a computer. The provisioning system is configured to carry out an inventive method for generating a surrogate marker based on medical image data.

An embodiment of the provisioning system provides that the computer is embodied for use of a trained function.

Functions, algorithms or parameters required for carrying out the inventive method can be provided to the provisioning system by way of the first and/or second interface. The biomarker and/or the first property and/or the second property and/or the first subregion and/or the second subregion and/or further results of an embodiment of the inventive method can be provided by way of the first and/or second interface. The provisioning system can be integrated into a medical imaging device, which medical imaging device is configured to acquire medical image data. The provisioning system can also be installed separately from the medical imaging device. The provisioning system can also be connected to the medical imaging device.

Embodiments of the inventive provisioning system are embodied analogously to the embodiments of the inventive method. The provisioning system can have further control components, which are required for carrying out an inventive method and/or are advantageous. The provisioning system can also be configured to send control signals and/or to receive and/or to process control signals in order to carry out an inventive method. Computer programs and further software can be stored on a storage unit of the provisioning system, by means of which the processor unit of the provisioning system controls and/or executes a process flow of an inventive method automatically.

An inventive computer program product can be loaded directly into a storage unit of a programmable computer and has program code means, in order to carry out an inventive method, if the computer program product is run in the computer. In this way, the inventive method can be implemented rapidly, exactly reproducibly and robustly. The computer program product is configured such that it can implement the inventive method steps by means of the computer. The computer must have the respective pre-conditions such as, for example, a suitable working memory store, a suitable graphics card or a suitable logic unit so that the respective method steps can be implemented efficiently. The computer program product is stored, for example, on an electronically-readable medium or is deposited on a network or server from where it can be loaded into the processor of a local provisioning system. Furthermore, control information of the computer program product can be stored on an electronically readable data carrier. The control information of the electronically readable data carrier can be configured such that they carry out a method according to the disclosure when the data carrier is used in a computer of the provisioning system. Examples of electronically readable data carriers are a DVD, a magnetic tape or a USB stick, on which electronically readable control information, in particular software, is stored.

Furthermore, the disclosure is based on an electronically readable data carrier, on which a program is stored, which is provided to carry out a method for generating a surrogate marker based on medical image data.

The advantages of the inventive provisioning system, the inventive computer program product and the inventive electronically readable data carrier essentially correspond to the advantages of the inventive method for generating a surrogate marker based on medical image data, which is detailed in advance. Features, advantages or alternative embodiments mentioned here can likewise also be transferred to the other subject matter and vice versa.

FIG. 1 shows a flow diagram of a first embodiment of an inventive method for generating a surrogate marker based on medical image data. The first embodiment provides that in method step 110 the medical image data is detected on the basis of a first interface 3, wherein the image data maps an image region. In method step 120 a first subregion of the image region is selected by segmenting a first structure included in the image region. In method step 130, a first property of the first subregion is then extracted. Based on the first property, in method step 140, the surrogate marker is determined, which is provided according to method step 150 on the basis of a second interface 4. At least one of the method steps 120, 130 and 140 is carried out on the basis of a computer 2.

The first embodiment can optionally comprise method step 160, a provisioning of a recommendation for a diagnosis and/or for a therapy and/or a probability for addressing a therapy based on the surrogate marker. The selection of the first subregion in method step 120 preferably comprises applying a trained function and/or a neural network and/or an active shape model and/or a level set method to the medical image data.

FIG. 2 shows a flow diagram of a second embodiment of an inventive method. This embodiment enables in particular longitudinal medical image data to be taken into account for determining the surrogate marker. For this purpose the second embodiment provides for detecting further medical image data mapping a further image region comprising the first structure on the basis of the first interface 2 according to method step 111. In method step 121, a second subregion of the further image region is selected by means of segmenting the first structure. In the following method step 131, a second property of the second subregion is extracted, which second property is taken into account when the surrogate marker is determined in the method step 140. The further image data have preferably been generated with a time lag with respect to the image data.

In an exemplary embodiment, the surrogate marker includes a ratio between the second property to the first property and/or a ratio between the first property and/or the second property to at least one threshold value.

FIG. 3 shows a flow diagram of a third embodiment of an inventive method. This embodiment enables in particular two structures which differ from one another to be taken into account in order to determine the surrogate marker. To this end, the third embodiment differs from the first embodiment therein in that in method step 122, a third subregion of the image region is selected by segmenting a second structure included in the image region. In the following method step 132, a third property of the third subregion is extracted, which third property is taken into account analogously to the first property when the surrogate marker is determined in method step 140.

The first subregion and the third subregion are preferably disjointed. The medical image data comprising the first structure and the medical image data comprising the second structure were preferably acquired on the basis of two recording methods which differ at least by means of a parameter. The surrogate marker, which was determined according to the third embodiment, comprises at least one of the following features:

ratio of the third property to the first property,
ratio of the first property and/or the third property to the at least one threshold value.

The third embodiment can optionally be combined with the second embodiment. In this case, the optional method steps 111, 121 and 131 can additionally be carried out and the second property in method step 140 can be taken into account when the surrogate marker is determined. In addition, in method step 123 a fourth subregion of the further image region can be selected by segmenting the second structure. In an optional method step 133, an extraction of a fourth property of the fourth subregion can take place, which fourth property can be taken into account in method step 140 when the surrogate marker is determined. In this embodiment, the further image data comprises the first structure and the second structure.

FIG. 4 shows an inventive provisioning system 1 in a schematic representation. The provisioning system 1 comprises a first interface 3, which is configured to detect medical image data, in other words to carry out method step 110, a second interface 4, which is configured to provide a surrogate marker, in other words to carry out method step 150, and a computer 2. In an exemplary embodiment, the computer 2 includes processor circuitry that is configured to perform one or more functions and/or operations of the computer 2. In this embodiment, one or more of the components of the computer 2 can include processor circuitry that is configured to perform the component(s) respective functions and/or operations. In an exemplary embodiment, the first interface 3 and/or the second interface 4 include processor circuitry that is configured to perform one or more respective functions and/or operations of the first interface 3 and the second interface 4.

In an exemplary embodiment, the computer 2 is configured to carry out the method steps 120, 130 and 140. For this purpose, the computer 2 can comprise a selector 21, which is configured to select a first subregion of the image region by means of segmenting a first structure included in the image region, in other words for carrying out method step 120. The computer 2 can also comprise an extractor 22, which is configured to extract a first property of the first subregion, in order words to carry out method step 130. The computer 2 can also comprise a determiner 23, which is configured to determine the surrogate marker based on the first property, in other words to carry out method step 140. In an exemplary embodiment, the selector 21, extractor 22, and/or determiner 23 includes processor circuitry that is configured to perform one or more respective functions and/or operations of the selector 21, extractor 22, and determiner 23.

In an exemplary embodiment, the provisioning system 1 together with the computer 2 is configured to generate a surrogate marker based on medical image data, in other words for carrying out the inventive method.

In an exemplary embodiment, the computer 2 includes computer programs and/or software, which can be directly loaded into a memory storage unit of the computer 2, not shown in further detail, having program means in order to carry out a method for generating a surrogate marker based on medical image data, if the computer programs and/or software are executed (e.g. by the processor) in the computer 2. In an exemplary embodiment, the computer 2 includes a processor, not shown in more detail, which is configured to execute the computer programs and/or software. Alternatively to this, the computer programs and/or software can also be stored on an electronically readable data carrier (e.g. external memory) 31 which is embodied separately from the provisioning system 1 and/or computer 2, wherein data access from the computer 2 to the electronically readable data carrier 31 can take place via a data network.

A method for generating a surrogate marker based on medical image data can also be present in the form of a computer program product, which implements the method on the computer 2 if it is carried out on the computer 2.

Similarly, an electronically readable data carrier 31 can exist with electronically readable control information stored thereupon, which comprises at least one such described computer program product and is embodied so that it carries out the described method when the data carrier 31 is used in a computer 2 of a provisioning system 1.

Although the disclosure has been illustrated and described in detail using the preferred exemplary embodiments, the disclosure is not limited by the disclosed examples, and a person skilled in the art can derive other variations therefrom that are still covered by the scope of protection of the disclosure.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for generating a surrogate marker based on medical image data mapping an image region, the method comprising:
   detecting the medical image data using a first interface;
   segmenting a first structure included in the image region to select a first subregion of the image region, the first structure including a liver, a spleen, a kidney, pancreas, or a substructure of the liver, the spleen, the kidney or pancreas;
   extracting a first property of the first subregion, the first property including a signal intensity within the first subregion, a volume of the first subregion, and a diffusion value within the first subregion;
   detecting, using the first interface, further medical image data mapping a further image region comprising the first structure, the further medical image data having been generated with a time lag of at least one month from the medical image data, wherein segmenting the first structure further selects a second subregion of the further image region;
   extracting a second property of the second subregion;
   determining the surrogate marker based on the first property and the second property; and
   providing the surrogate marker using a second interface.

2. The method as claimed in claim 1, wherein the selection of the first subregion takes place by applying, on the medical image data: a trained function, a neural network, an active shape model, and/or a level set method.

3. The method as claimed in claim 1, further comprising:
   provisioning, based on the surrogate marker, a recommendation for a diagnosis and/or for a therapy, and/or provisioning a probability for addressing a therapy based on the surrogate marker.

4. The method as claimed in claim 1, wherein the first structure further comprises:
   a prostate;
   a substructure of the prostate;
   a peripheral zone of the prostate; and/or
   a transition zone of the prostate.

5. The method as claimed in claim 1, wherein the surrogate marker comprises:
   a volume;
   a diameter;
   a threshold value for a diffusion value;
   threshold property;
   a spatial distribution of a texture; and/or
   a ratio of the first property to a threshold value.

6. The method as claimed in claim 1, wherein the surrogate marker comprises:
   a ratio of the second property to the first property; and/or
   a ratio of the first property and/or the second property to at least one threshold value.

7. The method as claimed in claim 1, further comprising:
   segmenting a second structure included in the image region to select a third subregion of the image region; and
   extracting a third property of the third subregion, wherein the determining the surrogate marker is further based on the third property.

8. The method as claimed in claim 7, wherein the first subregion and the third subregion are disjointed.

9. The method as claimed in claim 7, wherein the medical image data comprising the first structure and the medical image data comprising the second structure have been acquired using two recording methods, the two recording methods differing by at least one parameter.

10. The method as claimed in claim 7, wherein the surrogate marker comprises:
    a ratio of the third property to the first property; and/or
    a ratio of the first property and/or the third property to at least one threshold value.

11. A computer program product, embodied on a non-transitory computer-readable storage medium, that includes a program and is directly loadable into a memory of a programmable provisioning system, when the program is executed by the provisioning system, causes the provisioning system to perform the method for generating a surrogate marker as claimed in claim 1.

12. A non-transitory computer-readable storage medium with an executable program stored thereon, that when executed, instructs a processor to perform the method of claim 1.

13. A provisioning system comprising:
    a first interface configured to:
        detect medical image data, the medical image data mapping an image region, and
        detect further medical image data mapping a further image region, the further medical image data having been generated with a time lag of at least one month from the medical image data;
    a second interface; and
    a computer configured to:

segment a first structure included in the image region to select a first subregion of the image region and select a second subregion of the further image region, the first structure including a liver, a spleen, a kidney, pancreas, or a substructure of the liver, the spleen, the kidney or pancreas;

extract a first property of the first subregion, the first property including a signal intensity within the first subregion, a volume of the first subregion, and a diffusion value within the first subregion;

extract a second property of the second subregion;

determine a surrogate marker based on the first property and the second property; and provide the surrogate marker using the second interface.

14. The provisioning system as claimed in claim 13, wherein the computer is configured to use a trained function to perform the segmenting, extracting, determining, and providing.

15. The provisioning system as claimed in claim 13, wherein the providing of the surrogate marker comprises generating an electronic data signal corresponding to the surrogate marker and outputting the electronic data signal via the second interface.

16. The method as claimed in claim 1, wherein the surrogate marker comprises:
a threshold value for a diffusion value;
threshold property; and/or
a ratio of the first property to a threshold value.

17. The method as claimed in claim 1, further comprising associating the surrogate marker with other medical image data of one or more other examination objects, the other medical image data including the first property, wherein the one or more other examination objects are different from an examination object in which the medical image data is detected.

* * * * *